United States Patent

Kim et al.

Patent Number: 5,944,672
Date of Patent: Aug. 31, 1999

[54] DIGITAL HEARING IMPAIRMENT SIMULATION METHOD AND HEARING AID EVALUATION METHOD USING THE SAME

[75] Inventors: Dong-wook Kim, Sungnam; Young-cheol Park, Seoul, both of Rep. of Korea

[73] Assignee: Samsung Electronics Co., Ltd., Kyungki-do, Rep. of Korea

[21] Appl. No.: 09/060,257

[22] Filed: Apr. 15, 1998

[51] Int. Cl.$^6$ ........................................................ A61B 5/00
[52] U.S. Cl. ............................................. 600/559; 381/68
[58] Field of Search .................. 600/25, 559; 607/55–57; 381/60, 68

[56] References Cited

U.S. PATENT DOCUMENTS

| | | | |
|---|---|---|---|
| 5,016,280 | 5/1991 | Engebretson et al. | 381/68 |
| 5,276,739 | 1/1994 | Kroksted et al. | 381/68.2 |
| 5,475,759 | 12/1995 | Engebretson | 381/68.2 |
| 5,785,661 | 7/1998 | Shennib | 600/559 |

*Primary Examiner*—Max Hindenburg
*Attorney, Agent, or Firm*—Foley & Lardner

[57] ABSTRACT

A digital hearing impairment simulation method and a hearing aid evaluation method using the same are disclosed. According to the digital hearing impairment simulation method, a hearing characteristic table of a hearing impaired person is input and the input table is stored in a memory, in order to sample the hearing characteristics of the hearing impaired person (S1). A hearing loss table is calculated and stored in the memory (S2). An audio signal input via an audio input portion is converted to a digital signal and the converted digital signal is stored in the memory (S3). The converted digital signal is converted to the frequency domain signal using a fast Fourier transform algorithm (S4). The average power by critical band is calculated (S5). A hearing loss gain for each critical band is calculated using the hearing loss table and the average powers of the critical bands (S6). Coefficients for a digital filter corresponding to the hearing loss gains of the critical bands is calculated (S7). The input signal converted to a digital signal and stored in the memory in the step (S3) is digitally filtered using the digital filter coefficients (S8). The digitally filtered signal is converted to an analog signal and the converted analog signal is output to an audio output portion (S9). Thus, the performance of a hearing aid can be easily evaluated and hearing characteristics of a hearing impaired person can be easily sampled.

8 Claims, 5 Drawing Sheets

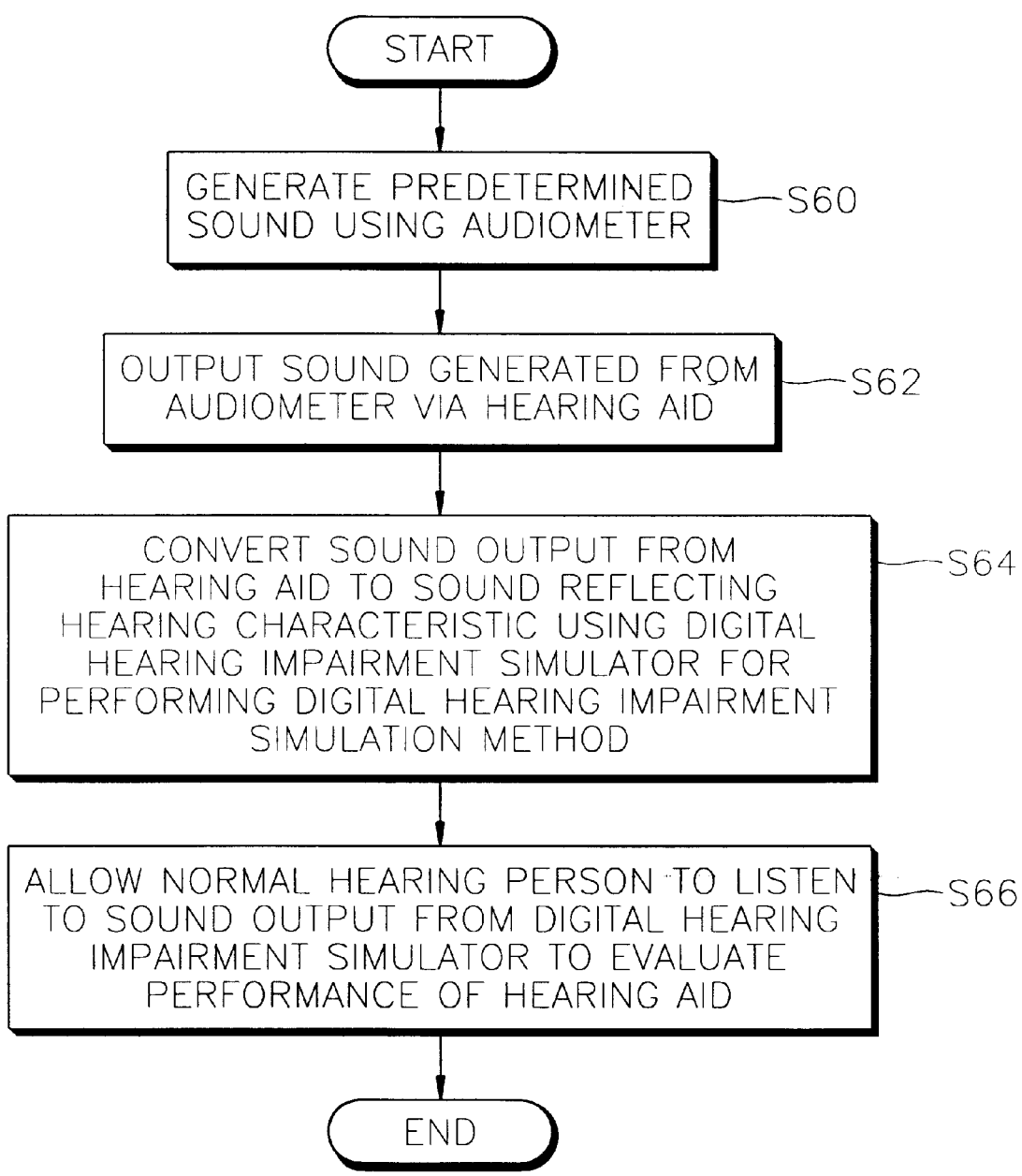

DIGITAL HEARING IMPAIRMENT SIMULATION METHOD AND HEARING AID EVALUATION METHOD USING THE SAME

BACKGROUND OF THE INVENTION

1. Field of the Invention

The present invention relates to a digital hearing impairment simulation method and a hearing aid evaluation method, and more particularly, to a digital hearing impairment simulation method and a hearing aid evaluation method using the same according to which a clinical test performed on actual hearing impaired persons can be replaced by one performed on normal persons, and also the performance of a hearing aid can be easily evaluated since the result of the clinical test is predictable.

2. Description of the Related Art

Generally, in a study of hearing impairment, or evaluation and comparison of hearing aids, a hearing test is directly performed on hearing impaired persons and a clinical test of wearing a hearing aid is performed. That is, in the clinical test, impaired persons are allowed to listen to diverse sounds or voice in a soundproof chamber or a hearing test room, and their responses to the sound or voice are checked and evaluated. However, since there are many types of hearing impairment, and the type of hearing impairment and characteristics of the individual vary greatly, experiments on hearing impairment must be performed based on an individual or the type of hearing impairment, which requires enormous time and effort. One method for evaluating the capability of a hearing aid is to evaluate the capability of the hearing aid itself, and another is to evaluate the hearing aid in use by directly applying the hearing aid to impaired persons. The method for evaluating a hearing aid in use has disadvantages in that: 1) a long-term test is not easy since most impaired persons are aged, 2) communication between hearing impaired persons and testers is not easy, 3) due to diverse hearing impairment types and the difference of individual hearing characteristics, it is difficult to group similar hearing impairments, and 4) impaired persons may respond uncertainly to the test due to symptoms of hearing impairment.

SUMMARY OF THE INVENTION

To solve the above problems, it is an objective of the present invention to provide a digital hearing impairment simulation method by which a clinical test performed on actual hearing impaired persons can be replaced by one performed on normal persons, and which makes it easy to evaluate the capability of a hearing aid since the result of the clinical test is predictable.

It is another objective of the present invention to provide a hearing aid evaluation method using the above digital hearing impairment simulation method.

Accordingly, to achieve the above objective, there is provided a digital hearing impairment simulation method which comprises the steps of: (S1) inputting a hearing characteristic table of a hearing impaired person and storing the input table in a memory, in order to model the hearing characteristics of the hearing impaired person; (S2) calculating a hearing loss table representing the difference between the hearing characteristic table of the hearing impaired person and a pre-stored hearing characteristic table of a normal person, and storing the calculated hearing loss table in the memory; (S3) converting an audio signal input via an audio input portion to a digital signal and storing the converted digital signal in the memory; (S4) converting the converted digital signal to the frequency domain signal using a fast Fourier transform algorithm; (S5) calculating an average power for each of critical bands of the signal converted to the frequency domain; (S6) calculating a hearing loss gain for each critical band, using the hearing loss table and the average powers of the critical bands; (S7) calculating coefficients for a digital filter corresponding to the hearing loss gains of the critical bands; (S8) digitally filtering the input signal converted to a digital signal and stored in the memory in the step (S3) using the digital filter coefficients; and (S9) converting the digitally filtered signal to an analog signal and outputting the converted analog signal to an audio output portion.

It is preferable in the present invention that the fast Fourier transform algorithm in the step (S4) is a 50% overlapped, 128 point fast Fourier transform algorithm having a sampling frequency of 12 kHz.

It is preferable in the present invention that the critical bands in the step (S5) are 20 bands increasing in size exponentially from a low frequency band to a high frequency band.

It is preferable in the present invention that the critical bands in the step (S5) are 20 ands increasing in size exponentially from a low frequency band to a high frequency band.

It is preferable in the present invention that the steps (S4) through (S9) are performed in units of a block consisting of 128 samples.

It is preferable in the present invention that the digital filter in the step (S8) is a frequency sampling filter.

To achieve the another objective of the present invention, there is provided a method for evaluating the performance of a hearing aid using a digital hearing impairment simulation method, the method comprising the steps of: (S1) generating predetermined sound using an audiometer which is a sound source; (S2) outputting the sound generated from the audiometer through the hearing aid; (S3) converting the sound output from the hearing aid to sound reflecting the hearing characteristic of a hearing impaired person using a digital hearing impairment simulator which performs a digital hearing impairment simulation method, and outputting the converted sound; and (S4) allowing a normal hearing person to listen to the sound output in step (S3) and checking the reaction of the listener to evaluate the performance of said hearing aid, in which the step (S3) includes the sub-steps of: (S3-1) inputting a hearing characteristic table of a hearing impaired person and storing the input table in a memory to model the hearing characteristic of the corresponding hearing impaired person; (S3-2) calculating a hearing characteristic table using the difference value obtained by comparing the hearing characteristic table of the hearing impaired person with that of a normal person which is previously stored and stored in the memory; (S3-3) inputting the audio signal output from the hearing aid to an audio input portion and converting the input signal to a digital signal and storing the same in the memory; (S3-4) converting the digital signal in step (S3-3) to a frequency domain using fast Fourier transform algorithm; (S3-5) calculating the average power by critical band of the signal which is converted to the frequency domain; (S3-6) calculating hearing loss gain using the hearing loss table and the average power by critical band; (S3-7) calculating a coefficient for a digital filer corresponding to the hearing loss gain by critical band; (S3-8) digitally filtering the signal converted to a digital signal and stored in the memory 16 in step (S3-3) using the coefficient for a digital filter; and (S3-9) converting the digitally filtered signal to an analog signal and outputting the converted signal to the audio output portion.

It is preferred in the present invention that, in the step (S4), the performance of the hearing aid is evaluated by measuring the sound output from the digital hearing impairment simulator using a measuring instrument.

BRIEF DESCRIPTION OF THE DRAWINGS

The above objective and advantages of the present invention will become more apparent by describing in detail a preferred embodiment thereof with reference to the attached drawings in which:

FIG. 6 is a flow chart for showing the hearing aid evaluation method using the digital hearing impairment simulation method according to the present invention.

DETAILED DESCRIPTION OF THE INVENTION

Generally, a sensorineural hearing impairment is generated by impairments to the sensory system and/or the nervous system, from the inner ear to the cerebral nervous system. Here, an audible level rises irregularly according to frequency, in a frequency range, and further an audible range differs according to the frequency unlike a conductive hearing impairment. In the present invention, the above sensorineural hearing impairment is an object of modeling. In order to give normal persons the effect of hearing impairment, input signals must be converted such that the hearing characteristics of normal persons are the same as those of hearing impaired persons. To do so, the gain applied to the input signals should be varied according to frequency and input level. Here, a process is needed to measure the input level according to the frequency and calculate non-linear gain according to the input levels by analyzing frequency spectrum. In the present invention, such a process is achieved by appropriately lowering the level of an input audio signal according to a critical band, by digital filtering.

Figure 1:
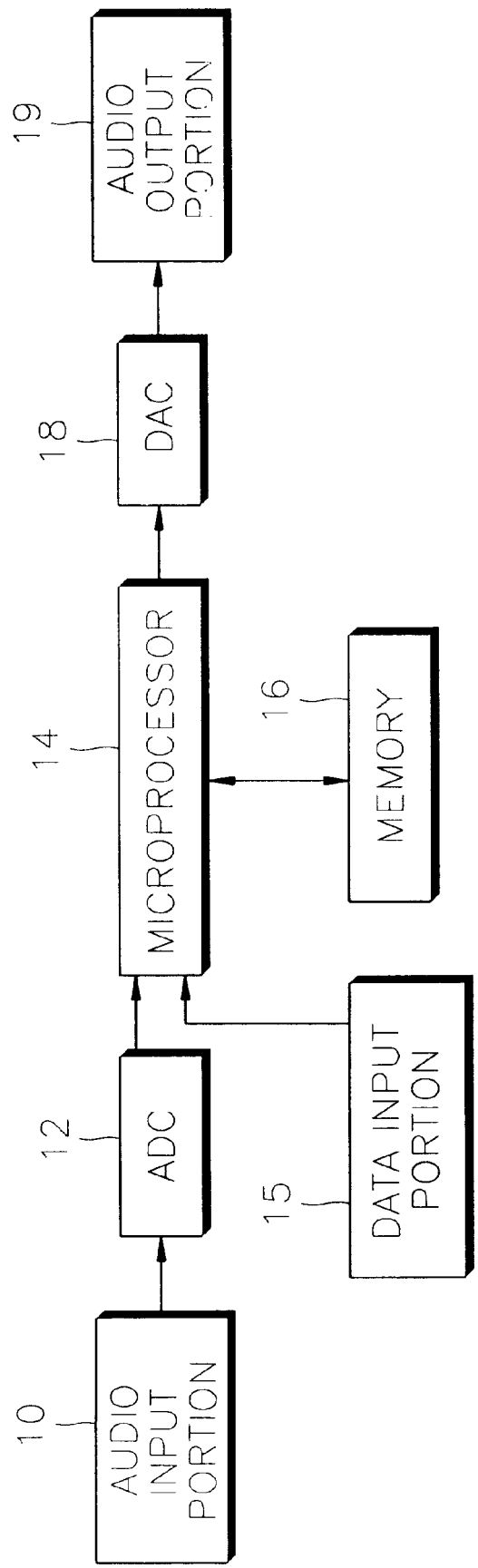
FIG. 1 is a block diagram showing a digital hearing impairment simulator for performing a digital hearing impairment simulation method according to the present invention.

FIG. 1 shows a digital hearing impairment simulator for performing a digital hearing impairment simulation method according to the present invention. Referring to the drawing, the digital hearing impairment simulator includes an audio input portion 10 for receiving an audio signal, an analog-to-digital converter (ADC) 12 for converting the output of the audio input portion 10 to a digital signal, a memory 16 for storing the digital hearing impairment simulation method according to the present invention and predetermined data, a microprocessor 14 for performing the digital hearing impairment simulation method stored in the memory 16, a data input portion 15 for receiving data from the outside, a digital-to-analog converter (DAC) 18 for converting the processed data to an analog signal, and an audio output portion 19 for converting the output of the DAC 18 to an audio signal. Here, a digital signal processor can be employed instead of the microprocessor 14.

Figure 2:
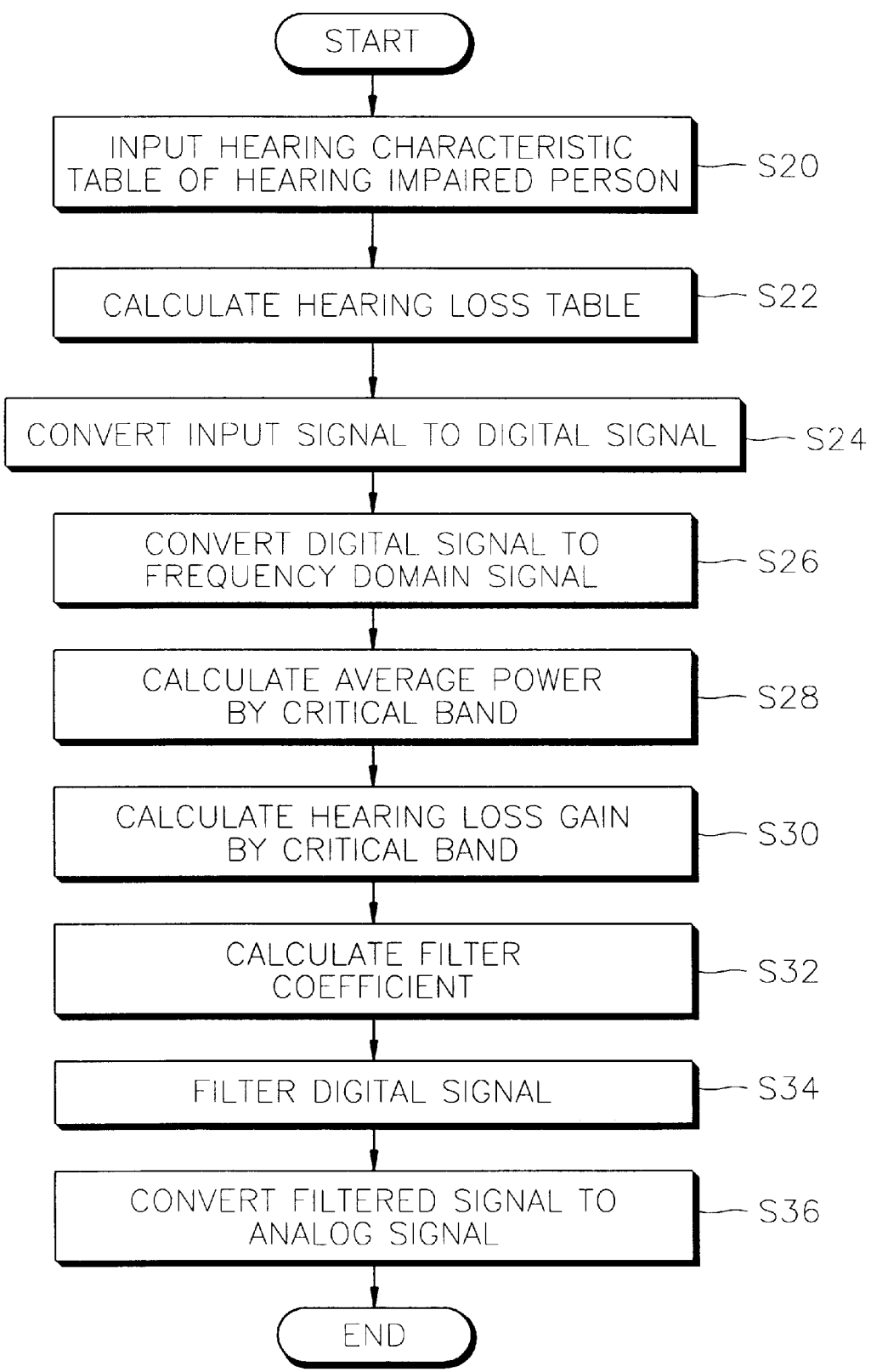
FIG. 2 is a flow chart for showing the digital hearing impairment simulation method according to a preferred embodiment of the present invention.

FIG. 2 shows the flow of the digital hearing impairment simulation method according to the present invention. The digital hearing impairment simulation method according to the present invention is stored in the memory 16 and performed by the microprocessor 14. The digital hearing impairment simulation method according to the present invention is largely comprised of a process of analyzing the frequency spectrum of an audio signal, a process of calculating hearing loss gain, and a process of filtering.

Referring to FIGS. 1 and 2, in a hearing characteristic table inputting step (S20), a user inputs a hearing characteristic table including hearing characteristic data of a hearing impaired person and stores the table in the memory 16. In a hearing loss table calculating step (S22), a hearing loss table is calculated using a hearing characteristic table of a normal person which is pre-stored and the hearing characteristic table of a hearing impaired person stored in the memory 16. The hearing loss table is stored in the memory 16. To transfer an audible range of a normal person to an audible range of a sensorineural hearing impaired person, a non-linear gain relationship between an input signal level and an output signal level at each frequency should be defined, and thus the phenomenon of decreasing the level of the input signal due to a hearing impairment is modeled in the present invention by introducing the concept of a hearing loss function.

Figure 3:
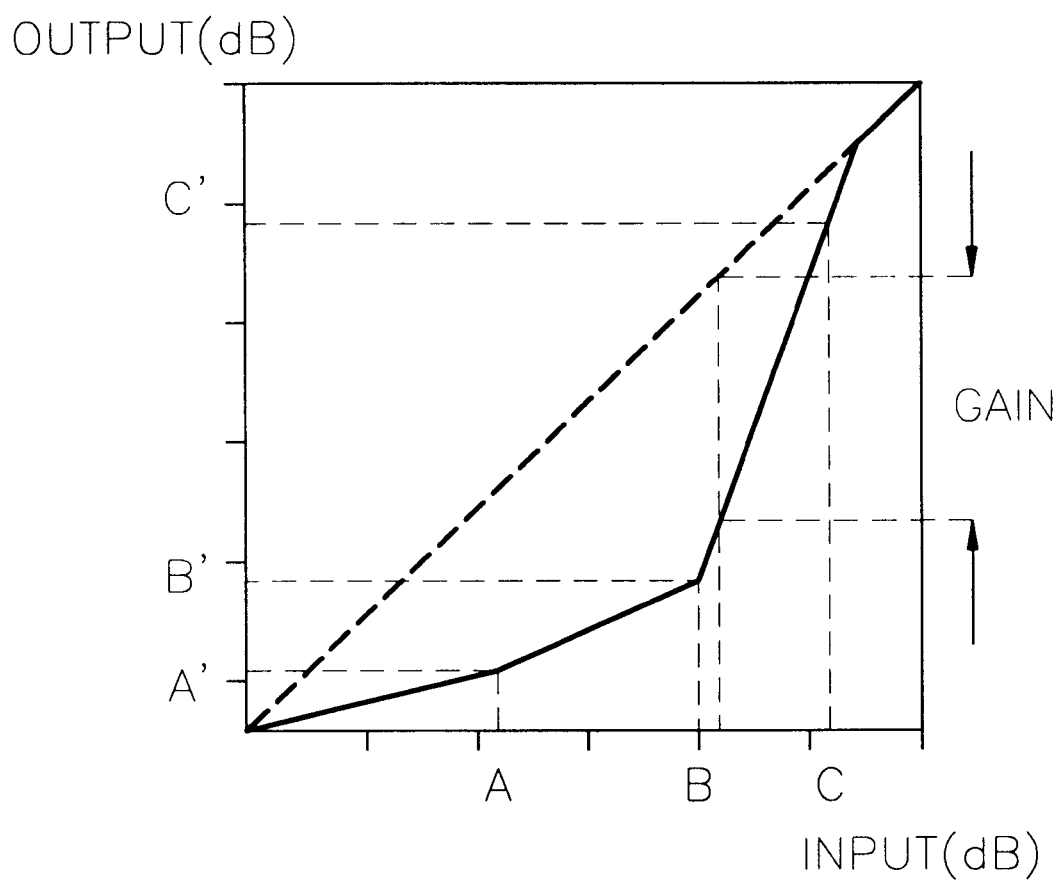
FIG. 3 is a graph representing a hearing loss function.

FIG. 3 is a graph showing a hearing loss function, representing a relationship between an input signal level and an output signal level with respect to a single frequency band. The hearing loss function is a concept similar to a loudness compensation function used in a digital hearing aid algorithm, but in the present invention, gain (GAIN) decreased by hearing loss of a hearing impaired person is calculated by defining an output signal level according to an input signal level, according to each frequency. As an input parameter for modeling a decreased audible range, the hearing loss function uses a minimum audible level showing a boundary of the audible band and an uncomfortable level (UCL). Also, a most comfortable level (MCL) is used as an input parameter for modeling an increased loudness of a sensorineural nervous hearing impaired person. Here, UCL is the level when sound begins to feel too loud and uncomfortable, and MCL is the level when sound feels most comfortable. Although information on equivalent loudness curves of hearing impaired persons and normal persons is required to make an ideal model of the loudness increase phenomenon, to measure this with respect to all frequencies and all levels is impossible. Further, since the loudness itself is based on the subjective sensation of each individual, an accurate measurement is difficult. MCL is widely known to have the characteristics of an equivalent loudness curve, in particular, to exhibit a relatively precise measurement that is availably in case of the sensorineural hearing impaired person having a narrow audible range, and thus, is used as a necessary parameter for the most efficient modeling of irregular loudness increase.

In an analog-to-digital conversion step (S24), the audio signal input to the audio input portion 10 is converted to a digital signal using the ADC 12 and the converted digital signal is stored in the memory 16. In a frequency domain conversion step (S26), the signal output from the ADC 12 is converted into the frequency domain signal using a fast Fourier transform algorithm, and in an average power by critical band calculation step (S28), the average power by a critical band is calculated with respect to the Fourier-transformed signal.

In the digital hearing impairment simulation method of the present invention, since each hearing loss gain differs according to the level of each frequency band of the input audio signal, it is important to accurately measure the level of each frequency band of the input signal. Thus, the input audio signal is sampled at 12 kHz by the ADC 12 and processed in blocks composed of 128 samples.

Also, since the blocks overlap by 50% to compensate for a transition period, the actual number of samples processed at each time is 64. The frequency spectrum analysis is made through a short-period (10.67 msec) fast Fourier transform algorithm using a Blackman window. The Blackman window has a side-lobe level which is quite small compared to other windows such as a hamming window or a hanning window. When the side-lobe level is high, an accurate level compensation is difficult since information of unrelated frequency bands is included. Particularly, in the case of audio signals, a high frequency component is often measured to be greater than the actual level, due to a low frequency component. The frequency spectrum obtained in the above manner is processed according to critical band units by applying a psychological sound model. The critical band is made as the human ear recognizes sound differently according to the frequency band like a filter bank.

Such a critical band unit is referred to as a bark and sound selection and audible limit are determined by the critical band. The size of the critical band increases approximately exponentially from a low frequency band to a high frequency band. Thus, the human ear is very sensitive to the sound of lower frequencies and less sensitive to the sound of higher frequencies. Therefore, the present invention adopts the concept of the critical band in order to efficiently model the human hearing characteristics. In the present digital hearing impairment simulation method, the frequency spectrum of an input audio signal is divided into 20 critical bands and the average power of each critical band is calculated.

In a hearing loss gain calculation step (S30), the hearing loss gain for each critical band is calculated, by applying the average power in the 20 critical bands calculated in step S28 to the hearing loss table obtained in step S22. Since all frequency components belonging to a single critical band have the same gain, each gain is obtained with respect to all frequency components.

In a filter coefficient calculation step (S32), a filter coefficient is calculated such that the digital filter has the correct hearing loss gain for each critical band, calculated in step S30. In a filtering step (S34), the input signal converted into a digital signal in step S24 and stored in the memory 16 is filtered using the filter coefficient obtained in step S32. In a digital-to-analog conversion step (S36), the digital signal filtered in step S34 is converted into an analog signal and output to the audio output portion 19.

When a general multi-channel filter is used, distortion between bands is high, and when more bands are used to improve resolution, the processing becomes complicated. Therefore, a frequency sampling filter is employed in the present invention. The frequency sampling filter has advantages in that the design of a filter to have an arbitrary response is easier than the design method using windows, since the filter coefficient is obtained from the amplitudes of points spaced apart by a predetermined distance on a frequency axis. In the present invention, the filter coefficient is newly calculated at every block and filtering is made by convolution. Here, 64 samples are actually filtered and processed among each of 128 samples.

Consequently, since the audio signal output from the audio output portion 19 is a distorted audio signal that a hearing impaired person hears, a normal person can hear as a hearing impaired person does. Thus, when the performance of a hearing aid is evaluated using the digital hearing impairment simulation method of the present invention, the result obtained from the test to a normal person is the same as that of the test to an actual hearing impaired person.

Figure 4:
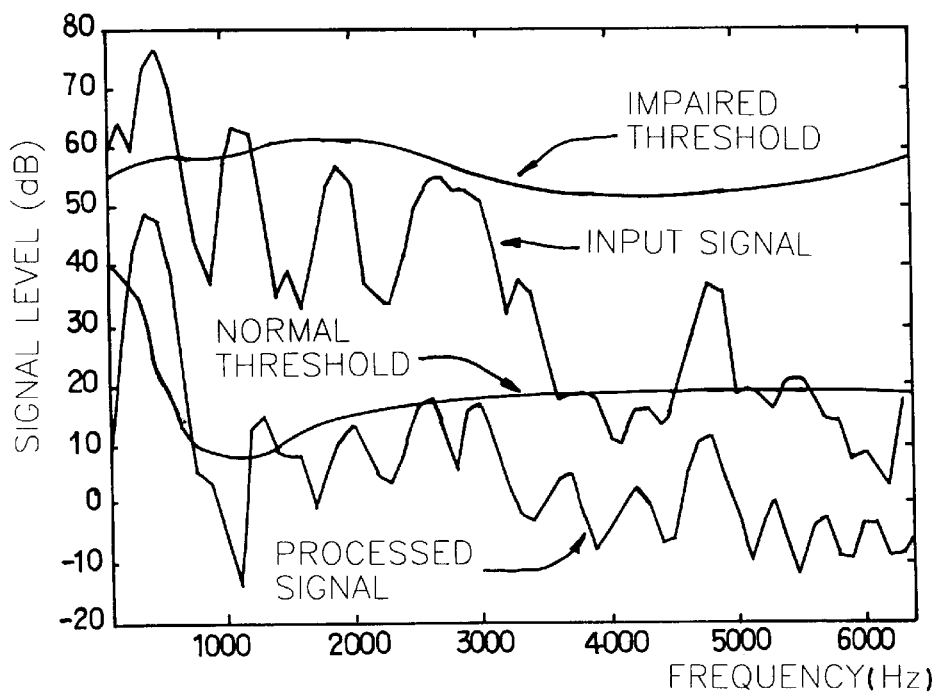
FIG. 4 is a graph representing the change of audio signal after performing the digital hearing impairment simulation method according to the present invention.

FIG. 4 shows the change of the audio signal after the digital hearing impairment simulation method according to the present invention is performed. Referring to FIG. 4, since the actually input audio signal is positioned over the normal threshold for the most part, a normal person can hear the audio signal. However, since the input audio signal is also positioned under the impaired threshold, a hearing impaired person can not hear the audio signal. When the digital hearing impairment simulation method is applied for the input audio signal, the audio signal is lowered under the audible limit level of a normal person so that the normal person hardly hear the input audio signal as a hearing impaired person does. Thus, an effect of modeling a normal person, without modeling a hearing impaired person, can be attained.

Figure 5:
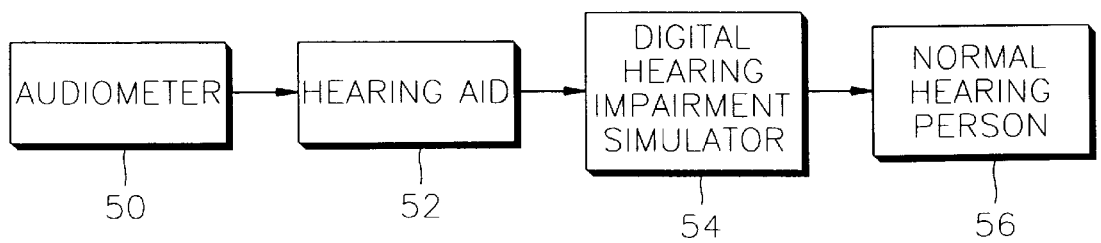
FIG. 5 is a diagram showing hardware for implementing a hearing aid evaluation method using the digital hearing impairment simulation method according to the present invention.

FIG. 5 shows hardware for explaining the hearing aid evaluation method using the digital hearing impairment simulation method according to the present invention. Referring to the drawing, the hardware is comprised of an audiometer 50 for generating sound, a hearing aid 52 for receiving the sound generated by the audiometer 50 and output the received sound, and a digital hearing impairment simulator 54 shown in FIG. 1 for receiving the sound output from the hearing aid 52 and performing the above-described digital hearing impairment simulation method. The sound output from the digital hearing impairment simulator 54 is listened to by a person having normal hearing capacity 56 and then the reaction to the sound is checked to evaluate the performance of the hearing aid 52. Here, instead of the normal hearing person 56, a measuring instrument for measuring the sound output from the digital hearing impairment simulator 54 can be used for evaluating the performance of the hearing aid 52.

FIG. 6 shows a method of evaluating a hearing aid using the digital hearing impairment simulation according to the present invention. Referring to FIGS. 5 and 6, predetermined sound is generated using the audiometer 50 which is a sound source (S60). The sound generated from the audiometer 50 is output through the hearing aid 52 (S62). The sound output from the hearing aid 52 is converted to sound reflecting the hearing characteristic of a hearing impaired person using the digital hearing impairment simulator 54 performing the above-described digital hearing impairment simulation method, and then is output (S64). The sound output in step S64 is listened to by the normal hearing person 56 to check the reaction of the listener, thereby evaluating the performance of the hearing aid 52 (S66).

The digital hearing impairment simulation method in step S64 is comprised of the sub-steps as follows. Referring to FIGS. 1 and 5 again, a hearing characteristic table of a hearing impaired person is input and stored in the memory 16 to model the hearing characteristic of the corresponding hearing impaired person (S1). A hearing characteristic table is calculated using the difference value obtained by comparing the hearing characteristic table of the hearing impaired person with that of a normal person which is previously stored and stored in the memory 16 (S2). The audio signal output from the hearing aid 52 is input to the audio input portion 10 and the input signal is converted to a digital signal and stored in the memory 16 (S3). The digital signal in step S3 is converted to a frequency domain using fast Fourier transform algorithm (S4). The average power by critical band of the signal which is converted to the frequency domain is calculated (S5). Hearing loss gain is calculated using the hearing loss table and the average power by critical band (S6). A coefficient for a digital filer corresponding to the hearing loss gain by critical band is calculated (S7). The signal converted to a digital signal and stored in the memory 16 in step S3 is digitally filtered using the coefficient for a digital filter (S8). The digitally filtered signal is converted to an analog signal and is output to the audio output portion 19 (S9).

As described above, in the hearing aid evaluation method using the digital hearing impairment simulation method according to the present invention, a clinical test performed on actual hearing impaired persons can be replaced by one performed on normal persons, and also the performance of a hearing aid can be easily evaluated since the result of the clinical test is predictable.

What is claimed is:

1. A digital hearing impairment simulation method comprising the steps of:
   (S1) inputting a hearing characteristic table of a hearing impaired person and storing the input table in a memory, in order to model the hearing characteristics of the hearing impaired person;
   (S2) calculating a hearing loss table representing the difference between the hearing characteristic table of the hearing impaired person and a pre-stored hearing characteristic table of a normal person, and storing the calculated hearing loss table in said memory;
   (S3) converting an audio signal input via an audio input portion to a digital signal and storing the converted digital signal in said memory;
   (S4) converting said converted digital signal to the frequency domain signal using a fast Fourier transform algorithm;
   (S5) calculating an average power for each of critical bands of said signal converted to the frequency domain;
   (S6) calculating a hearing loss gain for each critical band, using said hearing loss table and said average powers of the critical bands;
   (S7) calculating coefficients for a digital filter corresponding to said hearing loss gains of the critical bands;
   (S8) digitally filtering the input signal converted to a digital signal and stored in said memory in said step (S3) using said digital filter coefficients; and
   (S9) converting said digitally filtered signal to an analog signal and outputting the converted analog signal to an audio output portion.

2. The digital hearing impairment simulation method as claimed in claim 1, wherein said fast Fourier transform algorithm in said step (S4) is a 50% overlapped, 128 point fast Fourier transform algorithm having a sampling frequency of 12 kHz.

3. The digital hearing impairment simulation method as claimed in claim 1, wherein said critical bands in said step (S5) are 20 bands increasing in size exponentially from a low frequency band to a high frequency band.

4. The digital hearing impairment simulation method as claimed in claim 2, wherein said critical bands in said step (S5) are 20 bands increasing in size exponentially from a low frequency band to a high frequency band.

5. The digital hearing impairment simulation method as claimed in claim 1, wherein said steps (S4) through (S9) are performed in units of a block consisting of 128 samples.

6. The digital hearing impairment simulation method as claimed in claim 1, wherein said digital filter in said step (S8) is a frequency sampling filter.

7. A method for evaluating the performance of a hearing aid using a digital hearing impairment simulation method, said method comprising the steps of:
   (S1) generating predetermined sound using an audiometer which is a sound source;
   (S2) outputting the sound generated from said audiometer through said hearing aid;
   (S3) converting the sound output from said hearing aid to sound reflecting the hearing characteristic of a hearing impaired person using a digital hearing impairment simulator which performs a digital hearing impairment simulation method, and outputting the converted sound; and
   (S4) allowing a normal hearing person to listen to the sound output in step (S3) and checking the reaction of the listener to evaluate the performance of said hearing aid, wherein said step (S3) includes the sub-steps of:
   (S3-1) inputting a hearing characteristic table of a hearing impaired person and storing the input table in a memory to model the hearing characteristic of the corresponding hearing impaired person;
   (S3-2) calculating a hearing characteristic table using the difference value obtained by comparing the hearing characteristic table of the hearing impaired person with that of a normal person which is previously stored and stored in the memory;
   (S3-3) inputting the audio signal output from the hearing aid to an audio input portion and converting the input signal to a digital signal and storing the same in the memory;
   (S3-4) converting the digital signal in step (S3-3) to a frequency domain using fast Fourier transform algorithm;
   (S3-5) calculating the average power by critical band of the signal which is converted to the frequency domain;
   (S3-6) calculating hearing loss gain using the hearing loss table and the average power by critical band;
   (S3-7) calculating a coefficient for a digital filer corresponding to the hearing loss gain by critical band;
   (S3-8) digitally filtering the signal converted to a digital signal and stored in the memory in step (S3-3) using the coefficient for a digital filter; and
   (S3-9) converting the digitally filtered signal to an analog signal and outputting the converted signal to an audio output portion.

8. The method for evaluating the performance of a hearing aid using a digital hearing impairment simulation method as claimed in claim 7, wherein, in said step (S4), the performance of said hearing aid is evaluated by measuring the sound output from said digital hearing impairment simulator using a measuring instrument.

* * * * *

UNITED STATES PATENT AND TRADEMARK OFFICE
CERTIFICATE OF CORRECTION

PATENT NO. : 5,944,672 Page 1 of 1
APPLICATION NO. : 09/060257
DATED : August 31, 1999
INVENTOR(S) : Dong-wook Kim et al.

It is certified that error appears in the above-identified patent and that said Letters Patent is hereby corrected as shown below:

--[75] Inventors: Dong-wook Kim, Sungnam, Rep. of Korea; Young-cheol Park, Seoul, Rep. of Korea; Dong-ook Chung, Kyunggi; Won-ky Kim, Seoul, Rep. of Korea; Dae-hee Yoon, Seoul; Rep. of Korea --

Signed and Sealed this

Twenty-second Day of May, 2007

JON W. DUDAS
*Director of the United States Patent and Trademark Office*